United States Patent
Satyanarayana et al.

(10) Patent No.: US 11,576,917 B2
(45) Date of Patent: Feb. 14, 2023

(54) PHARMACEUTICAL COMPOSITIONS COMPRISING IBRUTINIB

(71) Applicant: Natco Pharma Limited, Hyderabad (IN)

(72) Inventors: Vattikuti Satyanarayana, Hyderabad (IN); Bhavanasi Krishna Murthy, Hyderabad (IN); Yalamanchalli Naveen Krishna, Hyderabad (IN); Bhat Pavan, Hyderabad (IN); Nannapaneni Venkaiah Chowdary, Hyderabad (IN)

(73) Assignee: NATCO PHARMA LIMITED, Hyderabad (IN)

(*) Notice: Subject to any disclaimer, the term of this patent is extended or adjusted under 35 U.S.C. 154(b) by 0 days.

(21) Appl. No.: 16/962,907

(22) PCT Filed: Jan. 11, 2019

(86) PCT No.: PCT/IN2019/050023
§ 371 (c)(1),
(2) Date: Jul. 17, 2020

(87) PCT Pub. No.: WO2019/142207
PCT Pub. Date: Jul. 25, 2019

(65) Prior Publication Data
US 2021/0060019 A1    Mar. 4, 2021

(30) Foreign Application Priority Data
Jan. 20, 2018  (IN) .............................. 201841002391

(51) Int. Cl.
*A61K 31/519* (2006.01)
*A61K 9/20* (2006.01)
*A61K 9/28* (2006.01)

(52) U.S. Cl.
CPC .......... *A61K 31/519* (2013.01); *A61K 9/2013* (2013.01); *A61K 9/2027* (2013.01); *A61K 9/2054* (2013.01); *A61K 9/2059* (2013.01); *A61K 9/2095* (2013.01); *A61K 9/2893* (2013.01)

(58) Field of Classification Search
None
See application file for complete search history.

(56) References Cited

U.S. PATENT DOCUMENTS

| | | |
|---|---|---|
| 7,514,444 B2 | 4/2009 | Honigberg et al. |
| 9,545,407 B2 | 1/2017 | Shu et al. |
| 9,655,857 B2 | 5/2017 | Chong et al. |
| 9,713,617 B2 | 7/2017 | Purro et al. |
| 2016/0256397 A1* | 9/2016 | Chong ................. A61K 9/2009 |
| 2016/0287594 A1 | 10/2016 | Gupta et al. |
| 2017/0252344 A1 | 9/2017 | Gupta et al. |
| 2017/0305919 A1 | 10/2017 | Purro et al. |

FOREIGN PATENT DOCUMENTS

| | | |
|---|---|---|
| IN | 599/CHE/2015 | 2/2017 |
| WO | WO-2016/022942 | 2/2016 |
| WO | WO-2016/088074 | 6/2016 |
| WO | WO-2016/105582 | 6/2016 |
| WO | WO-2016/164404 | 10/2016 |
| WO | WO-2017/125423 | 7/2017 |
| WO | WO-2017/125424 | 7/2017 |

OTHER PUBLICATIONS

International Search Report and Written Opinion for International PCT Application No. PCT/IN2019/050023, dated Mar. 20, 2019 (7 pages).

* cited by examiner

*Primary Examiner* — Aradhana Sasan
(74) *Attorney, Agent, or Firm* — Mintz Levin Cohn Ferris Glovsky and Popeo, P.C.

(57) ABSTRACT

The present invention relates to pharmaceutical compositions comprising Ibrutinib. More particularly, the present invention relates to a tablet composition comprising Ibrutinib and one or more pharmaceutically acceptable excipients and process for preparing such compositions.

7 Claims, No Drawings

PHARMACEUTICAL COMPOSITIONS COMPRISING IBRUTINIB

CROSS-REFERENCE TO RELATED APPLICATIONS

This application is a U.S. National Phase Application of PCT International Application No. PCT/IN2019/050023, filed on Jan. 11, 2019, which is an International Application of and claims the benefit of priority to Indian Patent Application No. 201841002391, filed on Jan. 20, 2018, each of which is incorporated herein in their entirety for all purposes.

FIELD OF THE INVENTION

The present invention relates to pharmaceutical compositions comprising Ibrutinib. More particularly, the present invention relates to a tablet composition comprising Ibrutinib and one or more pharmaceutically acceptable excipients and process for preparing such compositions.

BACKGROUND OF THE INVENTION

Ibrutinib is an inhibitor of Bruton's tyrosine kinase (BTK). It is chemically 1-[(3R)-3-[4-amino-3-(4-phenoxyphenyl)-1Hpyrazolo[3,4-d]pyrimidin-1-yl]-1-piperidinyl]-2-propen-1-one and is first disclosed in U.S. Pat. No. 7,514,444. Ibrutinib is used in the treatment of mantle cell lymphoma (MCL), chronic lymphocytic leukemia (CLL), small lymphocytic lymphoma (SLL), Waldenstrom's macroglobulinemia (WM), marginal zone lymphoma (MZL) and chronic graft-versus-host disease (cGVHD).

Ibrutinib is approved in the form of capsules and marketed by Pharmacyclics/Janssen under the brand name IMBRUVICA®. The capsules are approved in the strengths of 70 and 140 mg. The recommended dose of ibrutinib for the treatment of various diseases is 420 mg (three 140 mg capsules) orally once daily or 560 mg (four 140 mg capsules) orally once daily.

Ibrutinib is also approved in the form of tablets in the strengths of 140, 280, 420 and 560 mg and marketed by Pharmacyclics/Janssen under the brand name IMBRUVICA®.

U.S. Pat. No. 9,655,857 discloses a high-load solid tablet formulation comprising ibrutinib and one or more pharmaceutically acceptable excipients, wherein the high-load solid tablet formulation comprises at least 50% w/w of ibrutinib. It further discloses that the pharmaceutical composition comprises about 50% w/w to about 90% w/w of ibrutinib.

U.S. Pat. No. 9,545,407 discloses a solid dispersion formulation, wherein the formulation comprises a) about 49 to about 51% w/w of 50% active spray-dried ibrutinib, b) about 16 to about 18% w/w of lactose, c) about 24 to about 26% w/w of microcrystalline cellulose, d) about 5 to about 7% w/w of croscarmellose sodium, e) about 0.8 to about 1.2% w/w of colloidal silicon dioxide, and f) about 0.2 to about 0.8% w/w of magnesium stearate; and wherein the 50% active spray-dried ibrutinib is a spray-dried ibrutinib composition comprising about 50% w/w of ibrutinib dispersed into a polymer matrix; and the polymer in the polymer matrix is hydroxypropyl methyl cellulose acetate succinate (HPMCAS) or polyvinyl caprolactam-polyvinyl acetate-polyethylene glycol graft copolymer (Soluplus®).

U.S. Pat. No. 9,713,617 discloses a formulation for oral administration comprising (a) about 40 mgs to about 200 mgs of Ibrutinib; (b) about 40 wt % to about 50 wt % of a diluent; (c) about 3 wt % to about 10 wt % of a disintegrating agent; (d) about 2 wt % to about 7 wt % of a surfactant; and (e) about 0.2 wt % to about 1.0 wt % of a lubricant.

US 2016/0287594 discloses a pharmaceutical composition comprising Ibrutinib, a salt, prodrug, or metabolite thereof, microcrystalline cellulose, croscarmellose sodium, sodium lauryl sulfate, and magnesium stearate. It further discloses that the composition contains about 40 to about 45% by weight of Ibrutinib.

US 2017/0252344 discloses a pharmaceutical composition comprising Ibrutinib, a salt, prodrug, or metabolite thereof, microcrystalline cellulose, carboxymethylcellulose sodium, hydroxypropylmethylcellulose, citric acid monohydrate, disodium hydrogen phosphate, sucralose, sodium methyl parahydroxybenzoate, sodium ethyl parahydroxybenzoate, concentrated hydrochloric acid, sodium hydroxide, and water. It further discloses that the composition contains about 40 to about 45% by weight of Ibrutinib.

US 2017/0305919 formulation for oral administration comprising one or more pharmaceutically acceptable excipients and crystalline Form A of Ibrutinib.

WO 2017/125423 A1 discloses a pharmaceutical composition comprising ibrutinib, and wherein the pharmaceutical composition comprises i) at least 50% w/w of ibrutinib, and ii) excipients comprising about 10-30% w/w of filler, such as microcrystalline cellulose of the total weight of the pharmaceutical composition. It further discloses that the pharmaceutical composition comprises about 50% w/w to about 80% w/w of ibrutinib WO 2017/125424 A1 discloses a pharmaceutical composition comprising ibrutinib, and wherein the pharmaceutical composition comprises i) at least 60% w/w of ibrutinib, and ii) excipients comprising about 4-7% w/w of mannitol, and about 13-16% w/w of crospovidone of the total weight of the pharmaceutical composition. It further discloses that the pharmaceutical composition comprises about 60% w/w to about 80% w/w of ibrutinib.

WO 2016/088074 A1 discloses an amorphous solid dispersion comprising ibrutinib and one or more pharmaceutically acceptable carriers.

WO 2016/105582 A1 discloses a solid oral dosage form comprising (a) a compound that is an irreversible covalent kinase inhibitor, and/or a pharmaceutically acceptable salt thereof; (b) means for release of the compound and/or the pharmaceutically acceptable salt thereof in one or more mammalian intestinal sites selected from the jejunum and ileum and, (c) a pharmaceutically acceptable excipient.

IN 599/CHE/2015 A discloses a premix comprising amorphous ibrutinib and a pharmaceutically acceptable excipient.

The above prior art references discloses compositions comprising different concentrations of ibrutinib. However, there exists a need to develop a pharmaceutical composition which is more convenient and easier to swallow for providing the daily dose of Ibrutinib in a single dosage form when compared to the administration of 3 capsules or 4 capsules once daily. The inventors of the present invention have surprisingly found that a tablet composition comprising more than 90% w/w of ibrutinib and which is free of diluent shows better/comparable dissolution with respect to the marketed capsule or tablet dosage form of Ibrutinib. None of the above references disclose composition comprising ibrutinib more than 90% w/w of the composition. Further, the inventors also found that due to the presence of less excipients, the total weight as well as size of the tablets is reduced, which will be convenient for intake by the patients and leads to increase in patient compliance. The inventors also found that the tablet composition with reduced weight can be easily manufactured and had good tablet characteristics.

OBJECTIVE OF THE INVENTION

The main objective of the present invention relates to a composition comprising ibrutinib and one or more pharmaceutically acceptable excipients.

The present invention also relates to a tablet composition comprising ibrutinib and one or more pharmaceutically acceptable excipients.

The present invention also relates to a process for the preparation of a stable tablet composition comprising ibrutinib and one or more pharmaceutically acceptable excipients having comparable dissolution properties, content uniformity and equivalent bioavailability w.r.t marketed Ibrutinib dosage forms.

SUMMARY OF THE INVENTION

Accordingly, the present invention provides a composition comprising Ibrutinib and one or more pharmaceutically acceptable excipients.

The present invention also relates to a tablet composition comprising more than 90% w/w of Ibrutinib and one or more pharmaceutically acceptable excipients.

DETAILED DESCRIPTION OF THE INVENTION

The present invention also relates to a composition comprising ibrutinib and one or more pharmaceutically acceptable excipients.

The present invention also relates to a tablet composition comprising ibrutinib and one or more pharmaceutically acceptable excipients.

The present invention also relates a process for the preparation of composition comprising ibrutinib and one or more pharmaceutically acceptable excipients.

The present invention also relates a process for the preparation of tablet comprising ibrutinib and one or more pharmaceutically acceptable excipients.

In another embodiment, "Ibrutinib" according to the present invention includes but not limited to Ibrutinib and its pharmaceutically acceptable salts, ethers, esters, prodrugs, polymorphs and derivatives thereof.

As used herein, the term "% w/w" refers to the weight of the component based on the total weight of a composition comprising the component.

"Pharmaceutically acceptable excipient/s" are the components added to pharmaceutical formulation to facilitate manufacture, enhance stability, control release, enhance product characteristics, enhance bioavailability, enhance patient acceptability, etc.

In another embodiment, the composition according to the present invention further comprises one or more pharmaceutically acceptable excipients which include but not limited to diluents/fillers, disintegrants, binders, surfactants, glidants and lubricants. These excipients may be present intragranularly or extragranularly.

Diluents/filler according to the present invention include but not limited to lactose monohydrate, lactose anhydrous, fructose, dextrose, dextrates, dextrins, mannitol, lactitol, sorbitol, starch, sucrose, calcium carbonate, dibasic calcium phosphate, tribasic calcium phosphate, calcium sulfate, microcrystalline cellulose, silicified microcrystalline cellulose, cellulose powdered, kaolin and the like or combinations thereof.

Binders according to the present invention include but not limited to hydroxypropyl methylcellulose, hydroxypropyl cellulose, Polyvinylpyrrolidone (povidone), gelatin, ethyl cellulose, polyvinyl alcohol, pregelatinized starch, carboxymethyl cellulose, sodium alginate, microcrystalline cellulose and the like or combinations thereof.

Disintegrants according to the present invention include but not limited to starches or modified starches such as pregelatinized starch, croscarmellose sodium, crospovidone, sodium starch glycolate, low substituted hydroxypropyl cellulose, hydroxypropyl cellulose, microcrystalline cellulose and the like or combinations thereof.

Surfactants according to the present invention may be selected from anionic, cationic or non-ionic surface-active agents or surfactants. Suitable anionic surfactants include but not limited to carboxylate, sulfonate, and sulfate ions such as sodium lauryl sulfate (SLS), sodium laurate, dialkyl sodium sulfosuccinates particularly bis-(2-ethylhexyl) sodium sulfosuccinate, sodium stearate, potassium stearate, sodium oleate and the like. Suitable cationic surfactants include but not limited to those containing long chain cations, such as benzalkonium chloride, bis-2-hydroxyethyl oleyl amine or the like. Suitable non-ionic surfactants include but not limited to polyoxyethylene sorbitan fatty acid esters (polysorbates), fatty alcohols such as lauryl, cetyl and stearyl alcohols; glyceryl esters such as the naturally occurring mono-, di-, and tri-glycerides; fatty acid esters of fatty alcohols; polyglycolized glycerides such as gelucire; polyoxyethylene-polyoxypropylene block co-polymer such as Poloxamer and other alcohols such as propylene glycol, polyethylene glycol.

Lubricants/glidants according to the present invention include but not limited to colloidal silicon dioxide, stearic acid, magnesium stearate, calcium stearate, sodium stearyl fumarate, talc, hydrogenated castor oil, and mixtures thereof.

In one embodiment, the present invention relates to a process for the preparation of a pharmaceutical composition, comprising the steps of:
(i) blending Ibrutinib with one or more pharmaceutically acceptable excipients,
(ii) formulating the blend of step (i) into suitable dosage form.

In another embodiment, the present invention also relates to a process for the preparation of tablet composition, comprising the steps of:
(i) blending Ibrutinib with one or more pharmaceutically acceptable excipients,
(ii) compressing the blend of step (i) into tablet dosage form.

In another embodiment, the present invention further relates to a process for the preparation of tablet composition, comprising the steps of:
(i) blending Ibrutinib with one or more pharmaceutically acceptable excipients,
(ii) granulating the blend of step (i),
(iii) blending the granules of step (ii) with one or more pharmaceutically acceptable excipients, and
(iv) compressing the lubricated blend of step (iii) into tablet dosage form.

In another embodiment, the present invention further relates to a process for the preparation of tablet composition, comprising the steps of:

(i) blending Ibrutinib with one or more pharmaceutically acceptable excipients,
(ii) granulating the blend of step (i),
(iii) blending the granules of step (ii) with one or more pharmaceutically acceptable excipients,
(iv) compressing the lubricated blend of step (iii) into tablets, and
(v) optionally film coating the tablets obtained in step (iv).

In another embodiment, the present invention further relates to a process for the preparation of tablet composition, comprising the steps of:
(i) blending Ibrutinib with one or more pharmaceutically acceptable excipients,
(ii) granulating the blend of step (i),
(iii) blending the granules of step (ii) with one or more pharmaceutically acceptable excipients,
(iv) compressing the lubricated blend of step (iii) into tablets, and
(v) film coating the tablets obtained in step (iv).

In another embodiment, the present invention further relates to a tablet composition prepared by a process comprising the steps of:
(i) blending Ibrutinib with one or more pharmaceutically acceptable excipients,
(ii) granulating the blend of step (i),
(iii) blending the granules of step (ii) with one or more pharmaceutically acceptable excipients, and
(iv) compressing the lubricated blend of step (iii) into tablet dosage form.

In another embodiment, the present invention further relates to a tablet composition prepared by a process comprising the steps of:
(i) blending Ibrutinib with one or more pharmaceutically acceptable excipients,
(ii) granulating the blend of step (i),
(iii) blending the granules of step (ii) with one or more pharmaceutically acceptable excipients,
(iv) compressing the lubricated blend of step (iii) into tablets, and
(v) optionally film coating the tablets obtained in step (iv).

In another embodiment, the present invention further relates to a tablet composition prepared by a process comprising the steps of:
(i) blending Ibrutinib with one or more pharmaceutically acceptable excipients,
(ii) granulating the blend of step (i),
(iii) blending the granules of step (ii) with one or more pharmaceutically acceptable excipients,
(iv) compressing the lubricated blend of step (iii) into tablets, and
(v) film coating the tablets obtained in step (iv).

In another embodiment, the present invention relates to a process for the preparation of capsule composition, comprising the steps of:
(i) blending Ibrutinib with one or more pharmaceutically acceptable excipients, and
(iii) filling the blend of step (i) into capsules.

In another embodiment, the present invention relates to a process for the preparation of capsule composition, comprising the steps of:
(i) blending Ibrutinib with one or more pharmaceutically acceptable excipients,
(ii) lubricating the blended material of step (i) with a lubricant, and
(iii) filling the lubricated material of step (ii) into capsules.

In another embodiment, the pharmaceutical composition according to the present invention is in the form of tablets, capsules, granules, powder, pellets and sachets.

In another embodiment, the blend is formulated into a suitable dosage form like tablets or capsules using different techniques which are well known in the prior art.

In another embodiment, the compositions of the present invention may be prepared using any method known in the art, but are not limited to wet granulation, dry granulation, direct compression, melt granulation, solid dispersion and encapsulation.

In another embodiment, the solvents used for granulation process may be selected from water, isopropyl alcohol, methanol, ethanol, methylene chloride or combination thereof.

The composition according to the present invention may be uncoated or optionally coated with functional coating, film coating, moisture barrier coating or a protective coating composition. The coating may be selected from amongst one or more of those suitable coating materials known in the art. Coating may be performed by applying one or more film forming polymers, with or without other pharmaceutically inert excipients, as a solution/suspension using any conventional coating technique known in the art, such as spray coating in a conventional coating pan or fluidized bed processor or dip coating.

The amount of the film coating may be about 1 to about 10% w/w, preferably, about 1 to about 3% w/w, of the total composition. Any of a variety of film coatings can be used in the present composition. Suitable film coating may include but not limited to polymers, plasticizers, pigments, opacifiers, glidants, binders, antitacking agents, antifoaming agents, surfactants, fillers, extenders, coloring agents and the like.

Examples of film-forming polymers include ethylcellulose, hydroxypropyl methylcellulose, polyvinyl alcohol (PVA), hydroxypropylcellulose, methylcellulose, carboxymethyl cellulose, hydroxymethylcellulose, hydroxyethylcellulose, cellulose acetate, hydroxypropyl methylcellulose phthalate, cellulose acetate phthalate, cellulose acetate trimellitate; waxes such as polyethylene glycol; methacrylic acid polymers such as Eudragit® RL and RS; and the like. Alternatively, commercially available coating compositions comprising film-forming polymers marketed under various trade names, such as Opadry® may also be used for coating the tablets. The coating can be obtained as a dry blend concentrate.

The film coating may also optionally include a plasticizer such as triacetin, propylene glycol, diethyl phthalate, tributyl sebacate or polyethylene glycol (PEG), preferably PEG; and an anti-adherent or glidant such as talc, fumed silica or magnesium stearate, an opacifying agent such as titanium dioxide.

Coloring agent may be selected from FDA approved colorants such as Iron Oxide, Lake of Tartrazine, Allura Red, Lake of Quinoline Yellow, Lake of Erythrosine, Titanium Dioxide and the like.

The coating according to the present invention is applied by solubilising or suspending the excipients in solvents such as isopropyl alcohol, water, acetone, ethanol, methylene chloride, hydrochloric acid and the like, or mixtures thereof.

In one embodiment of the present invention, the composition comprises Ibrutinib in an amount of 50-95% w/w, preferably 80-95% w/w, more preferably 90-95% w/w of the composition.

In one preferred embodiment of the present invention, the composition comprises Ibrutinib in an amount of 90-95% w/w of the composition.

In another preferred embodiment, the tablet composition according to the present invention comprises more than 90% w/w of Ibrutinib and one or more pharmaceutically acceptable excipients.

In another embodiment, the pharmaceutical composition according to the present invention is in the form of tablets, preferably immediate release tablets.

In another embodiment, the tablet according to the present invention may be round or oval. The edges of the tablets can be beveled or rounded. In another embodiment, the tablets are ovoid or round. The tablets according to the invention may be scored.

In another preferred embodiment, the tablet composition according to the present invention is free of diluent or filler.

In another preferred embodiment, the present invention provides a tablet composition comprising more than 90% w/w of Ibrutinib and one or more pharmaceutically acceptable excipients, where in the tablet is free of diluent or filler.

In yet another embodiment, the present invention provides a composition comprising Ibrutinib in the range of about 10 mg to about 1000 mg.

In another embodiment of the present invention, the composition comprising Ibrutinib is administered to patients for the treatment of various diseases including but not limited to mantle cell lymphoma (MCL), chronic lymphocytic leukemia (CLL), small lymphocytic lymphoma (SLL), Waldenstrom's macroglobulinemia (WM), marginal zone lymphoma (MZL) and chronic graft-versus-host disease (cGVHD).

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1: Tablet Composition Comprising Ibrutinib

| S. No | Ingredients | Quantity per tablet mg | % w/w |
|---|---|---|---|
| | Intragranular | | |
| 1 | Ibrutinib | 560.00 | 93.33 |
| 2 | Croscarmellose sodium | 20.00 | 3.33 |
| 3 | Povidone | 16.00 | 2.66 |
| 4 | Purified water | q.s | — |
| | Extragranular | | |
| 5 | Sodium stearyl fumarate | 4.00 | 0.66 |
| | Total Tablet weight | 600.00 | 100.00 |

The processing steps involved in manufacturing the tablets of Ibrutinib were given below:
(i) Ibrutinib and croscarmellose sodium were sifted and blended,
(ii) binder solution was prepared by dissolving povidone in purified water,
(iii) the blend of step (i) was granulated using binder solution of step (ii) and dried,
(iv) the dried granules of step (iii) were sifted and lubricated with Sodium stearyl fumarate,
(v) the lubricated granules of step (iv) were compressed into tablets.

Example 2: Tablet Composition Comprising Ibrutinib

| S. No | Ingredients | Quantity per tablet mg | % w/w |
|---|---|---|---|
| | Intragranular | | |
| 1 | Ibrutinib | 560.00 | 90.32 |
| 2 | Croscarmellose sodium | 20.00 | 3.23 |
| 3 | Povidone | 16.00 | 2.58 |
| 4 | Purified water | q.s | — |
| | Extragranular | | |
| 5 | Croscarmellose sodium | 20.00 | 3.23 |
| 6 | Sodium stearyl fumarate | 4.00 | 0.65 |
| | Total Tablet weight | 620.00 | 100.00 |

Example 3: Tablet Composition Comprising Ibrutinib

| S. No | Ingredients | Quantity per tablet mg | % w/w |
|---|---|---|---|
| | Intragranular | | |
| 1 | Ibrutinib | 560.00 | 90.32 |
| 2 | Croscarmellose sodium | 20.00 | 3.23 |
| 3 | Povidone | 16.00 | 2.58 |
| 4 | Purified water | q.s | — |
| | Extragranular | | |
| 5 | Pregelatinized starch | 20.00 | 3.23 |
| 6 | Sodium stearyl fumarate | 4.00 | 0.65 |
| | Total Tablet weight | 620.00 | 100.00 |

Example 4: Tablet Composition Comprising Ibrutinib

| S. No | Ingredients | Quantity per tablet mg | % w/w |
|---|---|---|---|
| | Intragranular | | |
| 1 | Ibrutinib | 560.00 | 93.33 |
| 2 | Povidone | 16.00 | 2.67 |
| 3 | Purified water | q.s | — |
| | Extragranular | | |
| 4 | Sodium lauryl sulfate | 20.00 | 3.33 |
| 5 | Magnesium stearate | 4.00 | 0.67 |
| | Total Tablet weight | 600.00 | 100.00 |

The compositions given in examples 2-4 were prepared using similar procedure described in Example 1.

Dissolution Data:

Table 1 given below provides the comparative dissolution profile of Ibrutinib tablets prepared according to Examples 1-4 with IMBRUVICA® 560 mg tablets and 4×140 mg capsules of IMBRUVICA® carried out in 900 ml of 0.1N HCl as dissolution medium in USP II apparatus (paddle) at 75 rpm.

TABLE 1

Comparative dissolution profile of Ibrutinib 560 mg tablets prepared according to Examples 1-4 with IMBRUVICA® 560 mg tablets and 4 × 140 mg capsules of IMBRUVICA®

| Time (in min) | 4 × 140 mg capsules of IMBRUVICA® | IMBRUVICA® 560 mg tablets | Ex-1 | Ex-2 | Ex-3 | Ex-4 |
|---|---|---|---|---|---|---|
| 5 | 57.1 | 37.0 | 70.7 | 72.8 | 73.7 | 25.1 |
| 10 | 70.7 | 69.0 | 89.5 | 90.1 | 90.9 | 39.5 |
| 15 | 73.8 | 81.8 | 96.7 | 97.6 | 97.3 | 50.0 |
| 20 | 75.4 | 87.1 | 100.1 | 101.0 | 99.7 | 56.6 |
| 30 | 76.1 | 91.4 | 102.6 | 103.3 | 102.5 | 65.3 |
| 45 | 77.0 | 94.1 | 103.5 | 105.7 | 104.7 | 72.9 |

We claim:

1. A tablet composition comprising:
   (a) more than 90% w/w and 95% w/w or less of Ibrutinib,
   (b) povidone as a binder,
   (c) one or more disintegrants selected from the group consisting of pregelatinized starch and croscarmellose sodium, and
   (d) sodium stearyl fumarate as a lubricant,
   and wherein the composition is free of a diluent.

2. The tablet composition as claimed in claim 1, wherein the composition is prepared by wet granulation.

3. The tablet composition as claimed in claim 1, wherein the composition is prepared by a process comprising the steps of:
   i) blending Ibrutinib with one or more pharmaceutically acceptable excipients,
   ii) granulating the blend of step (i),
   iii) blending the granules of step (ii) with one or more pharmaceutically acceptable excipients,
   iv) compressing the lubricated blend of step (iii) into tablets, and
   v) optionally film coating the tablets obtained in step (iv).

4. The tablet composition as claimed in claim 1, wherein the composition is prepared by a process comprising the steps of:
   i) blending Ibrutinib with povidone and one or more disintegrants selected from the group consisting of pregelatinized starch and croscarmellose sodium,
   ii) granulating the blend of step (i),
   iii) blending the granules of step (ii) with sodium stearyl fumarate and optionally one or more disintegrants selected from the group consisting of pregelatinized starch and croscarmellose sodium,
   iv) compressing the lubricated blend of step (iii) into tablets, and
   v) optionally film coating the tablets obtained in step (iv).

5. A tablet composition comprising:
   (i) an intragranular portion comprising:
      (a) 93.33% w/w of Ibrutinib,
      (b) 3.33% w/w of croscarmellose sodium,
      (c) 2.66% w/w of povidone,
   (ii) an extragranular portion comprising:
      (d) 0.66% w/w of sodium stearyl fumarate, and
   wherein the composition is free of a diluent.

6. A tablet composition comprising:
   (i) an intragranular portion comprising:
      (a) 90.32% w/w of Ibrutinib,
      (b) 3.23% w/w of croscarmellose sodium,
      (c) 2.58% w/w of povidone,
   (ii) an extragranular portion comprising:
      (d) 3.23% w/w of croscarmellose sodium,
      (e) 0.65% w/w of sodium stearyl fumarate, and
   wherein the composition is free of a diluent.

7. A tablet composition comprising:
   (i) an intragranular portion comprising:
      (a) 90.32% w/w of Ibrutinib,
      (b) 3.23% w/w of croscarmellose sodium,
      (c) 2.58% w/w of povidone,
   (ii) an extragranular portion comprising:
      (d) 3.23% w/w of pregelatinized starch,
      (e) 0.65% w/w of sodium stearyl fumarate, and
   wherein the composition is free of a diluent.

* * * * *